(12) United States Patent
Roger

(10) Patent No.: US 8,070,821 B2
(45) Date of Patent: Dec. 6, 2011

(54) HYBRID FEMORAL IMPLANT

(75) Inventor: Christopher Abee Roger, Waldwick, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1236 days.

(21) Appl. No.: 11/318,820

(22) Filed: Dec. 27, 2005

(65) Prior Publication Data
US 2007/0150067 A1  Jun. 28, 2007

(51) Int. Cl.
*A61F 2/40* (2006.01)

(52) U.S. Cl. .................... 623/20.17; 623/20.14

(58) Field of Classification Search .......... None
See application file for complete search history.

(56) References Cited

U.S. PATENT DOCUMENTS

| | | | |
|---|---|---|---|
| 4,193,140 A | 3/1980 | Treace | |
| 4,215,439 A | 8/1980 | Gold et al. | |
| 4,551,863 A | 11/1985 | Murray | |
| 4,659,331 A | 4/1987 | Matthews et al. | |
| 4,714,473 A | 12/1987 | Bloebaum | |
| 4,938,769 A | 7/1990 | Shaw | |
| 4,944,756 A | 7/1990 | Kenna | |
| 5,080,674 A | 1/1992 | Jacobs et al. | |
| 5,108,435 A | 4/1992 | Gustavson et al. | |
| 5,116,375 A * | 5/1992 | Hofmann | 623/20.27 |
| 5,171,282 A | 12/1992 | Pequignot | |
| 5,198,432 A | 3/1993 | Fariss | |
| 5,358,529 A | 10/1994 | Davidson | |
| 5,443,518 A | 8/1995 | Insall | |
| 5,480,444 A | 1/1996 | Incavo et al. | |
| 5,531,793 A | 7/1996 | Kelman et al. | |
| 5,549,688 A | 8/1996 | Ries et al. | |
| 5,683,471 A | 11/1997 | Incavo et al. | |
| 5,683,472 A | 11/1997 | O'Neil et al. | |
| 5,702,460 A | 12/1997 | Carls et al. | |
| 5,755,803 A | 5/1998 | Haines et al. | |
| 6,010,366 A | 1/2000 | Tanigawa et al. | |
| 6,059,831 A * | 5/2000 | Braslow et al. | 128/898 |

(Continued)

FOREIGN PATENT DOCUMENTS
EP    738503    10/1996

OTHER PUBLICATIONS

Catalog page for Scorpio PS Posteriorly Stabilized Single Axis Knee Femoral Components, p. 3.

*Primary Examiner* — David Isabella
*Assistant Examiner* — Joshua Levine
(74) *Attorney, Agent, or Firm* — Lerner, David, Littenberg, Krumholz & Mentlik, LLP

(57) ABSTRACT

A hybrid prosthetic femoral component has an outer bearing surface for engaging a tibial bearing and an inner surface for engaging a prepared distal femur. The inner surface having a distal surface, an anterior surface and a posterior surface, wherein said posterior surface has a first surface structure for allowing tissue ingrowth and the anterior and distal surfaces having a second surface structure for contacting bone cement. The first and second structure have different surface characteristics with different properties wherein the first surface structure is a porous surface and the second surface is a non-porous textured surface. The hybrid prosthetic femoral component further comprises an anterior chamfered surface and a posterior chamfered surface wherein the posterior chamfered surface includes the first surface structure and the anterior chamfered surface includes the second surface structure.

10 Claims, 3 Drawing Sheets

U.S. PATENT DOCUMENTS

| | | |
|---|---|---|
| 6,080,196 A | 6/2000 | Bertin |
| 6,165,223 A | 12/2000 | Metzger et al. |
| 6,168,629 B1 | 1/2001 | Timoteo |
| 6,171,340 B1 | 1/2001 | McDowell |
| 6,214,051 B1 | 4/2001 | Badorf et al. |
| 6,224,632 B1 | 5/2001 | Pappas et al. |
| 6,325,828 B1 | 12/2001 | Dennis et al. |
| 6,402,786 B1 | 6/2002 | Insall et al. |
| 6,413,279 B1 | 7/2002 | Metzger et al. |
| 6,589,283 B1 | 7/2003 | Metzger et al. |
| 6,599,322 B1 | 7/2003 | Amrich et al. |
| 6,652,586 B2 | 11/2003 | Hunter et al. |
| 6,749,638 B1 | 6/2004 | Saladino |
| 6,770,099 B2 | 8/2004 | Andriacchi et al. |
| 2002/0016635 A1 | 2/2002 | Despres et al. |
| 2003/0065401 A1 | 4/2003 | Amrich et al. |
| 2003/0153977 A1 | 8/2003 | Suguro et al. |
| 2003/0181984 A1* | 9/2003 | Abendschein ............ 623/20.19 |
| 2003/0225457 A1 | 12/2003 | Justin et al. |
| 2004/0054417 A1 | 3/2004 | Soffiati et al. |
| 2004/0210316 A1 | 10/2004 | King et al. |
| 2005/0010301 A1 | 1/2005 | Disilvestro et al. |
| 2005/0010302 A1 | 1/2005 | Dietz et al. |
| 2005/0021147 A1 | 1/2005 | Tarabichi |
| 2005/0043807 A1 | 2/2005 | Wood |
| 2005/0085815 A1 | 4/2005 | Harms et al. |

\* cited by examiner

HYBRID FEMORAL IMPLANT

BACKGROUND OF THE INVENTION

The present invention relates to an orthopedic implant, more particularly to a femoral component for a knee prosthesis. The femoral component has three inside surfaces opposite the bearing surface of the femoral component with at least a posterior surface of the femoral component having a porous coating for tissue in-growth.

In order to treat arthritic knees with prosthetic knee implants surgeons have performed total knee arthroplasty (TKA) in which a tibial component, a femoral component and a patella component are implanted onto a surgically prepared tibia, femur and patella. With regard to the femoral component, typically at least three resected surfaces are formed on the distal femur. These surfaces are the posterior, distal and anterior surfaces of the femur. Typically these cuts are planar, although in some situations, the posterior surface may be rounded. In addition to the posterior, anterior and distal surfaces of the femur, two additional resections may be performed, namely, an anterior chamfer cut and a posterior chamfer cut. If the latter two resections are made, then there are typically five planar surfaces which engage corresponding inner surfaces on the femoral component.

Fixation of the tibial, femoral and patellar component to the resected bone surfaces typically involves the use of bone cement or natural bone tissue in-growth. Knee replacement prostheses designed to be fixated through bone in-growth typically have a porous layer to facilitate the bone in-growth. Such a layer is shown in U.S. Pat. No. 4,550,448 in which two layers of uniform beads are utilized to induce the tissue in-growth. These beads may be coated with an osteoinductive and/or osteoconductive coating. An osteoinductive coating may be a bone morphogenic protein such as OP-1 sold by Stryker Corporation. Osteoconductive coatings might be a calcium phosphate coating, either plasma sprayed or applied by the process of U.S. Pat. No. 5,164,187. Both osteoinductive and osteoinductive materials can be used in combination and can include other therapeutic agents, such as antibiotics, analgesics and other water-soluble agents. Alternately, bone cement may be utilized to fix the prosthesis on the resected distal femur. Such a cement is SIMPLEX® P bone cement sold by Stryker Corporation. Often textured surfaces are formed on the implant in areas which contact bone cement. Such textured surfaces may be in a waffle pattern or patterns with undercuts which allow the bone cement to interdigitate with the implant.

SUMMARY OF THE INVENTION

It is one aspect of the present invention to provide a hybrid femoral component for a knee replacement prosthesis that includes a combination of two or more different surface textures on the at least three and preferably five surfaces that contact the resected distal femur. Preferably, the two different surface textures can include surfaces for receiving bone cement and surfaces for promoting tissue in-growth. Such bone surfaces can come in many varieties including hydroxyapatite coated, waffle or porous beaded structures or a smooth surface for cement. Having both cement accepting surfaces and surfaces for promoting tissue in-growth on a single femoral component but in different areas eases both the implantation and the possible future removal of the implant.

Preferably surfaces for accepting bone cement fixation would be present on the inner surfaces of the implant which contact the anterior and distal resected femoral portions. If the anterior surface includes an anterior chamfer resection and corresponding surface on the femoral component, this would also be preferably designed to be used with cement. Thus, a posterior chamfer surface would be coated with a preferably porous tissue in-growth surface.

It is another aspect of the present invention to eliminate the need for bone cement to be applied to the posterior region of the implant. It is often difficult for the surgeon to detect the presence of loose cement particles that flow out of the region between the implant and the resected knee during implantation of the implant onto the distal femur. When a femoral component is prepared for cement implantation, its inside surfaces (those contacting the bone) are covered with bone cement in an amount to ensure full area coverage of the bone cement onto the femoral component and distal femur. When this prepared component is impacted onto the bone, some bone cement may seep out which is then removed by the surgeon. However, it is difficult to see this bone cement seepage on the posterior aspect of the implant. This is especially true if a minimally invasive surgical procedure is utilized, which procedures limit the length of the incision made in the anterior femur. Thus eliminating the bone cement from the posterior and posterior chamfer surface, if present, eliminates the seepage problem in this area.

Using a hybrid femoral component design in which at least one in-growth surface is preferably used on the inner posterior surfaces of the implant also benefits a press-fit implantation when the bone cuts are not made perfectly. The bone cement in the anterior region of the implant will fill in any gaps that are present between the implant and the resected bone. This packed cement will help to ensure a press-fit between the implant and the resected bone in the posterior region of the implant.

Thus it is an additional aspect of the invention to provide bone tissue in-growth surfaces on the inner posterior surfaces of the implant, bone cement contacting surfaces on the distal and anterior side of the implant which bone cement surfaces may either be smooth or textured to couple with bone cement applied thereto.

These and other aspects of the invention are provided by a hybrid prosthetic femoral component comprising an outer bearing surface for engaging a tibial bearing and an inner surface for engaging a repaired distal femur, the inner surface having a distal surface, an anterior surface, and a posterior surface, wherein the posterior surface has a first coating for allowing tissue in-growth, and the anterior and distal surfaces have a second coating for contacting bone cement. Typically the first and second coatings have different surface characteristics and different porosities. However, it may be possible to use a porous surface both on the anterior and distal surfaces. Preferably the first coating is a porous tissue in-growth surface, and the second coating is a nonporous textured surface, for example, having a waffle pattern. The hybrid prosthetic femoral component may additionally include an anterior chamfer surface and a posterior chamfer surface wherein the posterior chamfer surface includes the first tissue in-growth coating and the anterior chamfer surface includes a coating adapted for use with bone cement. While the anterior surfaces may have a porous surface texture, they could also be nonporous and, in fact, be smooth. In the preferred embodiment the distal surface has a textured surface or smooth surface for accepting cement. Alternately, tissue in growth surface can be used distally. The anterior and anterior chamfer and distal inner surfaces may be recessed with the textured surface extending outwardly from the recess portion. The recess portion may include a waffle or dimpled textured thereon. The tissue in-growth surface of the posterior and posterior chamfer areas may include a beaded porous coating or may be plasma-sprayed metal, such as titanium or even a porous surface produced by selective laser sintering (SLS) as taught in U.S. patent application Ser. Nos. 10/704,270 (2004/0191106) and 11/027,421.

The invention also contemplates the method of implanting the femoral component which includes applying a liberal amount of bone cement to the anterior, anterior chamfer and distal surface of a typical femoral component with the posterior chamfer and posterior surfaces not being covered by the bone cement. The surgeon then impacts the implant onto the resected distal femur and cleans any remaining cement that was pushed out during implantation. The cement will only be present around the anterior and distal portions of the implant, which is highly visible to the surgeon. The more difficult to see posterior chamfer and posterior surface of the implant can be ignored by the surgeon with respect to excess bone cement.

DETAILED DESCRIPTION

Figure 1:
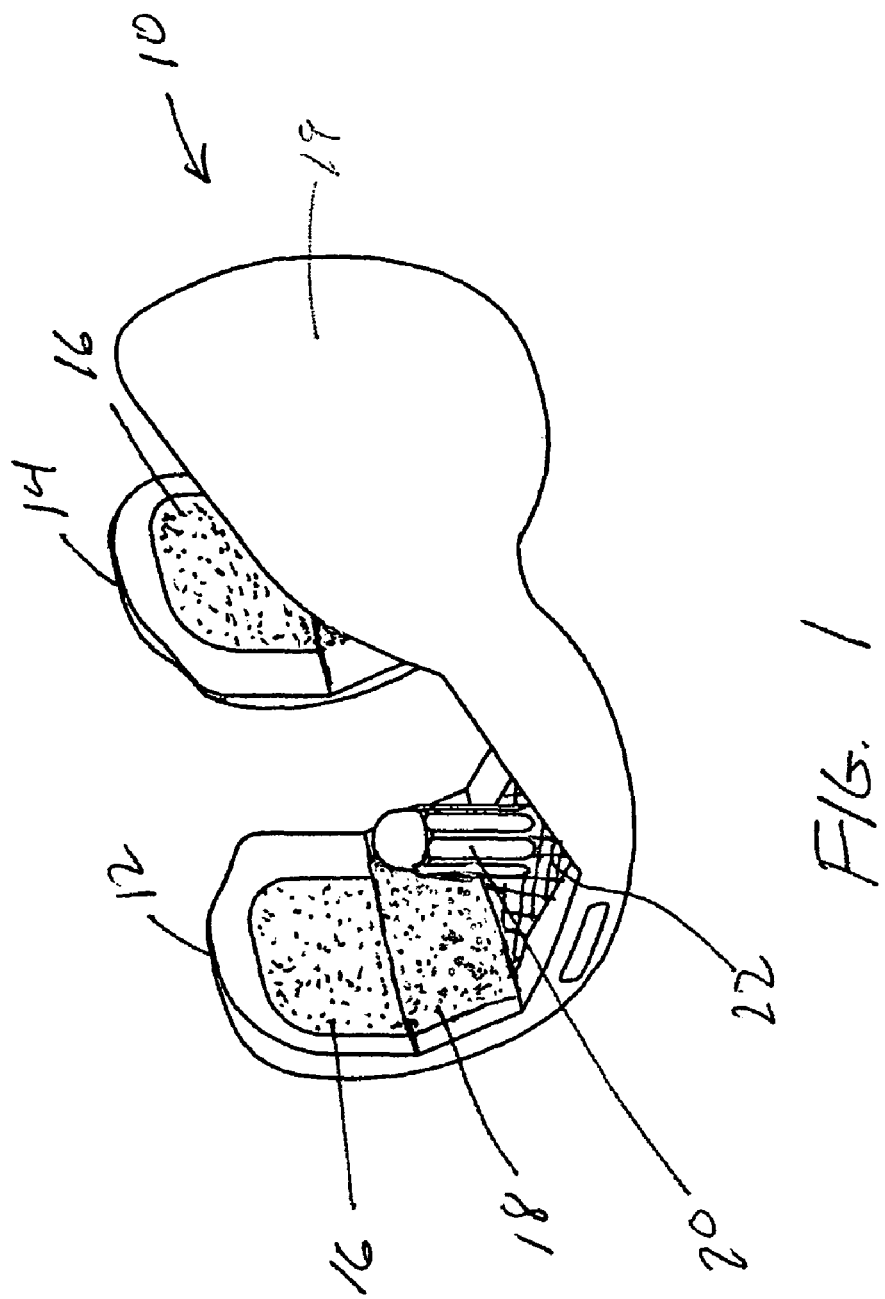
FIG. 1 is an isometric view of the femoral component of the present invention viewed from the anterior medial side.

Referring to FIG. 1, there is shown the femoral component of the present invention generally denoted as 10 with anterior outer surface 19. The view shown is from the anterior medial side looking back toward the posterior condyles 12 and 14, respectively. As can be seen, the posterior condyles 12 and 14 include an inner posterior surface 16 and an inner posterior chamfer surface 18. Also shown is a fixation peg 20 which can be of any typical design. The distal surface 22 is also shown.

Figure 2:
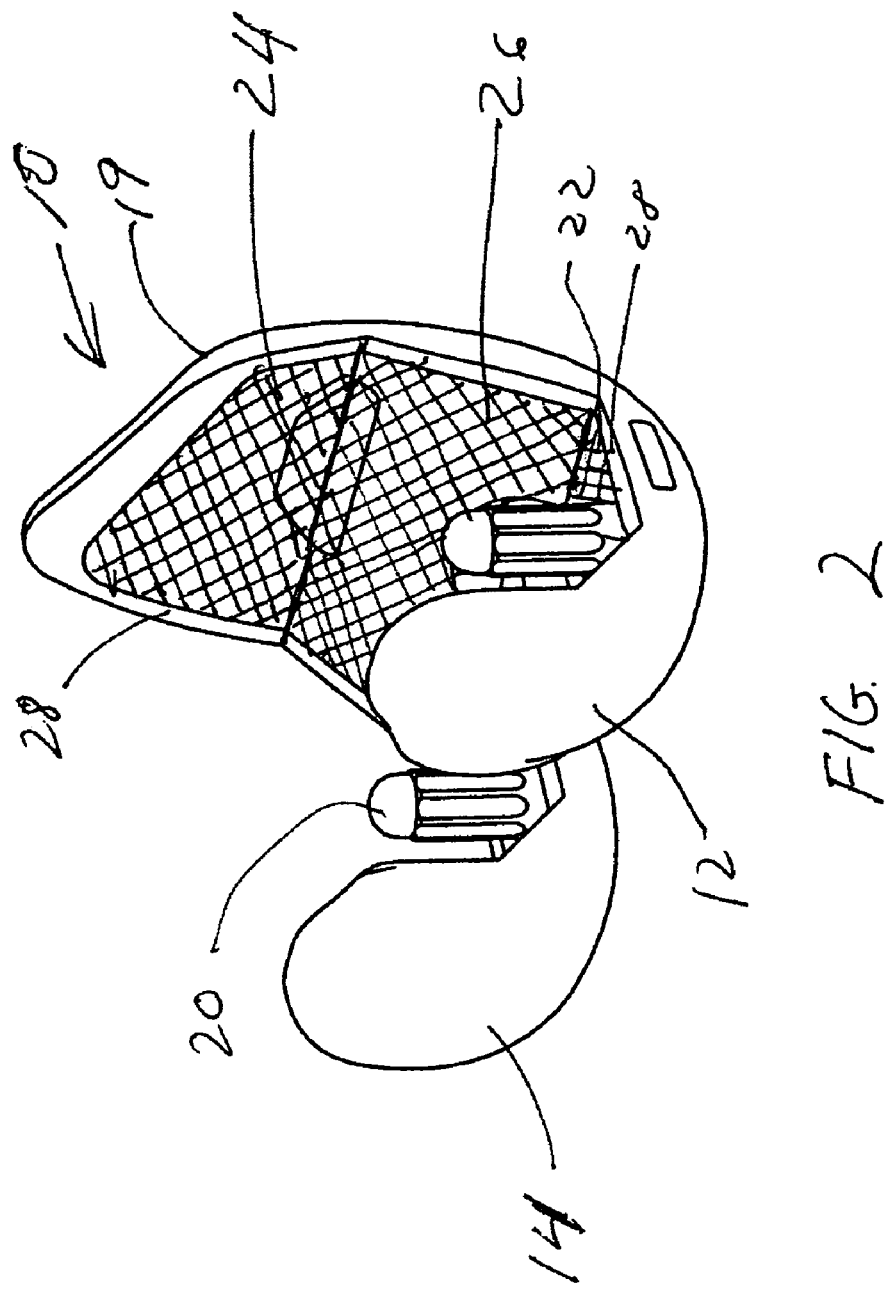
FIG. 2 is an isometric view of the femoral component of the present invention viewed from the posterior medial side.

Referring to FIG. 2, there is shown an isometric view looking from the posterior medial side which shows the anterior inner surface 24 and the anterior chamfer surface 26 along with both posterior condyles 12 and 14. In this view, both the medial and lateral pegs 20 are shown. Preferably, surfaces 22, 24 and 26 have a waffle pattern and are preferably recessed slightly so that the waffle pattern does not extend above the edge surfaces 28 surrounding the anterior and anterior chamfer surfaces and the distal surface 22. The implant shown in FIGS. 1 and 2 is a left femoral component with condyle 14 being the lateral condyle.

Figure 3:
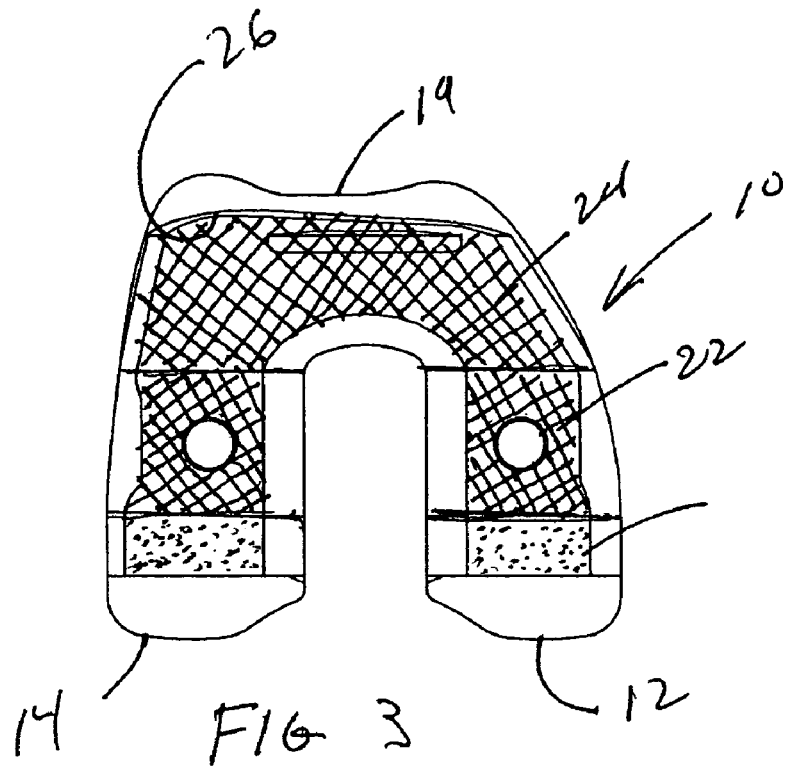
FIG. 3 is a top view of the femoral components of FIGS. 1 and 2.
Figure 4:
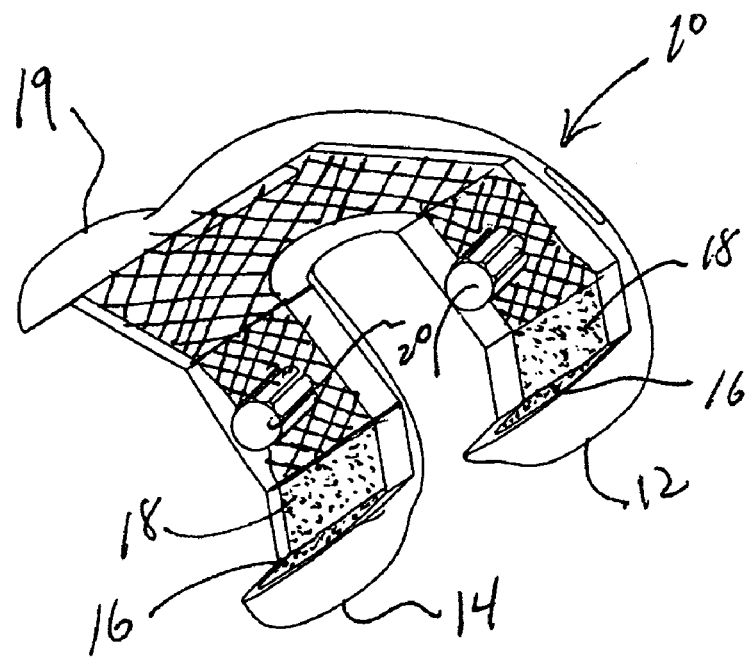
FIG. 4 is a top view of the femoral component at an angle with respect to the anterior side thereby showing the posteriors condylar portions of the implant.

Referring to FIGS. 3 and 4, there is shown top views of the femoral component 10 of FIGS. 1 and 2 with the waffle surface 22, 24, 26 on the distal, anterior and anterior chamfer surfaces. Porous surfaces 16 and 18 are best shown in FIG. 4.

In the preferred embodiment, the porous coating on the posterior and posterior chamfer surfaces is a beaded coating produced by U.S. Pat. No. 4,550,448. Fibrous mesh in-growth surfaces such as those disclosed in U.S. Pat. No. 4,479,271 or the plasma-sprayed titanium surface of U.S. Pat. No. 3,605,123 may also be utilized. The waffle pattern utilized on the anterior, anterior chamfer and distal surfaces may be that used on the SCORPIO® CR femoral component sold by Stryker Corporation. As stated above, it is also possible just to have a smooth or merely roughened surface on the bone cement receiving anterior, anterior chamfer and distal surfaces.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A hybrid prosthetic femoral component comprising:
   a body having an outer bearing surface for sliding engagement with a tibial bearing, the outer surface includes an anteriorly facing surface, a distally facing surface and a posteriorly facing surface;
   the body having an inner surface for engaging a prepared distal femur, said body inner surface having a proximally facing surface opposite the body distally facing outer surface for mounting on a distal femur surface, a body posteriorly facing inner surface opposite the body outer anteriorly facing surface for mounting on an anterior femur surface and body inner anteriorly facing surface opposite the body posteriorly facing outer surface for directly contacting a posterior femur surface, wherein said body inner anteriorly facing surface for directly contacting the posterior femur surface has a first non-waffle pattern porous structure for allowing tissue ingrowth and said inner posteriorly facing and inner proximally facing surfaces for respectively mounting on the anterior and distal femur surface has a second non-porous waffle pattern structure for contacting bone cement; and
   the inner surface of the body further comprising a posteriorly facing chamfered surface for mounting on an anterior chamfered surface of the femur and an anteriorly facing chamfered surface for contacting a posterior chamfered inner surface of the femur wherein said anteriorly facing chamfered surface of the hybrid prosthetic femoral component body includes said first porous structure and said posteriorly facing chamfered inner surface includes said second non-porous waffle pattern structure.

2. The hybrid prosthetic femoral component as set forth in claim 1 wherein the anterior, anterior chamfer and distal inner surfaces of the body have a recessed portion.

3. The hybrid prosthetic femoral component as set forth in claim 1 wherein said first porous structure of said femoral component body anteriorly facing chamfer inner surface and said anteriorly facing inner surface is a porous structure formed by beads.

4. The hybrid prosthetic femoral component as set forth in claim 3 wherein the beaded surface has a hydroxyapatite coating.

5. A hybrid prosthetic femoral component comprising:
   an outer bearing surface for engaging a tibial bearing, the outer surface includes an anteriorly facing surface, a distally facing surface and a posteriorly facing surface; and
   an inner surface for mating with a prepared distal femur, said inner surface having a proximally facing surface opposite the distally facing outer surface, a posteriorly facing surface opposite the anteriorly facing outer surface, an anteriorly facing surface opposite the posteriorly facing outer surface, a posteriorly facing chamfered surface and an anteriorly facing chamfered surface, the inner surfaces respectively mating with a distal surface, an anterior surface, a posterior surface, an anterior chamfered surface and a posterior chamfered surface of the prepared femur wherein said femoral component inner anteriorly facing surface and said inner anteriorly facing chamfered surface have a first non-waffle pattern porous structure for allowing tissue ingrowth and said inner proximally facing surface, inner posteriorly facing surface and inner posteriorly facing chamfered surface have a second non-porous waffle structure for contacting bone cement.

6. The hybrid prosthetic femoral component as set forth in claim 5 wherein said femoral component inner posteriorly facing surface, inner chamfer surface and inner proximally facing surface have a recessed portion with a defining edge surface adjacent to said first and said second structures.

7. The hybrid prosthetic femoral component as set forth in claim 5 wherein the anteriorly facing surface and anteriorly facing chamfer surface have a beaded tissue ingrowth coating.

8. The hybrid prosthetic femoral component as set forth in claim 7 wherein the beaded surface includes a hydroxyapatite coating.

9. The hybrid prosthetic femoral component as set forth in claim 6 wherein said defining edge surfaces have a non-textured surface.

10. The hybrid prosthetic femoral component as set forth in claim 1 wherein the inner proximally facing surface, the inner anteriorly facing surface, and the inner anteriorly facing chamfered surface are each surrounded by an edge surface extending above the waffle pattern.

* * * * *

UNITED STATES PATENT AND TRADEMARK OFFICE
CERTIFICATE OF CORRECTION

PATENT NO.        : 8,070,821 B2                                    Page 1 of 1
APPLICATION NO.   : 11/318820
DATED             : December 6, 2011
INVENTOR(S)       : Christopher Abee Roger It is certified that error appears in the above-identified patent and that said Letters Patent is hereby corrected as shown below:

Column 4, line 21, "and body" should read --and a body--.

Signed and Sealed this
Twelfth Day of March, 2013

Teresa Stanek Rea
*Acting Director of the United States Patent and Trademark Office*